(12) United States Patent
Paulson

(10) Patent No.: US 8,098,063 B2
(45) Date of Patent: Jan. 17, 2012

(54) UNTETHERED, UNPOWERED, ROLLABLE DEVICE TO SENSE CONDITION OF PIPELINE WALL

(75) Inventor: Peter O. Paulson, Calgary (CA)

(73) Assignee: Pure Technologies Ltd., Calgary, Alberta (CA)

( * ) Notice: Subject to any disclaimer, the term of this patent is extended or adjusted under 35 U.S.C. 154(b) by 919 days.

(21) Appl. No.: 11/814,921

(22) PCT Filed: Feb. 7, 2006

(86) PCT No.: PCT/CA2006/000146
§ 371 (c)(1),
(2), (4) Date: Feb. 11, 2008

(87) PCT Pub. No.: WO2006/081671
PCT Pub. Date: Aug. 10, 2006

(65) Prior Publication Data
US 2008/0204008 A1 Aug. 28, 2008

(30) Foreign Application Priority Data
Feb. 7, 2005 (CA) ...................................... 2496150

(51) Int. Cl.
*G01N 27/72* (2006.01)
(52) U.S. Cl. .......................................... 324/220; 73/592
(58) Field of Classification Search .......... 324/220–221; 73/592
See application file for complete search history.

(56) References Cited

U.S. PATENT DOCUMENTS

| 5,672,967 A | 9/1997 | Jensen et al. |
| 6,241,028 B1 | 6/2001 | Bijleveld et al. |
| 2005/0145018 A1* | 7/2005 | Sabata et al. .................. 73/49.1 |

FOREIGN PATENT DOCUMENTS

| CN | 1305564 A | 7/2001 |
| EP | 1494005 | 5/2005 |
| WO | 01/70422 | 9/2001 |
| WO | 2004/059274 A2 | 7/2004 |

* cited by examiner

*Primary Examiner* — Jay Patidar
(74) *Attorney, Agent, or Firm* — Blake, Cassels & Graydon LLP; Daphne L. Maravei

(57) ABSTRACT

A sensor unit for use in sensing conditions in a pipeline comprises an untethered a ball-shaped surround adapted to roll along the interior surface of a pipeline, and instrument package within the ball-shaped surround. The package contains at least one magnetometer or accelerometer. Preferably, three magnetometers, arranged orthogonally, are present. Other sensors can also be present as required, such as an acoustic sensor to detect leaks and a temperature or chemical sensor. Recording means record the data acquired by the magnetometer(s) or accelerometer and the sensors, and optionally also record a timing trace.

17 Claims, 14 Drawing Sheets

UNTETHERED, UNPOWERED, ROLLABLE DEVICE TO SENSE CONDITION OF PIPELINE WALL

BACKGROUND OF THE INVENTION

1. Field of the Invention

This invention relates to a detector for the detection of anomalies in pipelines which transport liquids. In its preferred embodiment, the invention relates to a sensor unit which is capable of inspecting a liquid-transporting pipeline, without interfering with the transported liquids in the pipeline. In one embodiment, the detector locates liquid leaks where liquid is escaping from the pipeline from the pipeline. In another embodiment, the detector is used in a concrete pipeline with wire reinforcement, and detects corroded or damaged portions of the wire reinforcement, or is used in a metal pipeline and detects corrosion and/or weld failures. The sensor unit also has a novel way of determining its location within the pipeline.

2. Description of the Prior Art

It is known to use acoustic detectors to detect leaks in a pipeline. Detectors can, for example, be placed on the underside of inspection ports, or they can be placed along a cable strung between inspection ports, or along a cable allowed to trail along the lowest portion of the pipe, as shown in Paulson Canadian Patent no. 2,273,979. Such detectors can detect the sound made by a breaking wire reinforcement in a wire-reinforced concrete pipeline, or can detect the sound of liquid escaping through a leak in a metal or concrete pipeline.

It is known to inspect small diameter pipelines, particularly oil pipelines, using a device called a "pig", which fills the pipeline and is propelled along it by oil pressure. Such inspection can be used to locate leaks and to check the welds between adjacent lengths of pipe.

It is also known to inspect pipelines with a neutral density untethered sensor, which is propelled by the liquid of the pipeline, such as is shown in PCT Published Application WO 2004/059274. However, it is difficult to tell the location of such a sensor within the pipeline, and the sensor is subject to getting trapped within the pipeline. Further, such sensor units communicate with electromagnetics, which prevents it from using magnetic sensors such as magnetometers to sense pipeline conditions.

If a pipeline is large enough (for example, large concrete pipes to bring water to cities or large sewer pipes) the pipe can be drained and a human can conduct a manual inspection. Some types of inspection are also known in drained pipelines using sensors mounted on a wheeled cart or the like. See for example, Paulson U.S. Pat. No. 6,781,369.

SUMMARY OF THE INVENTION

The present invention provides a self-contained sensor unit, which is released into the pipeline at one manhole or inspection port, while the pipeline is transporting liquid. The sensor unit travels with the flow of the liquid, and is recoverable at a downstream inspection port or other location where convenient access to the pipe can be obtained. It contains at least one magnetometer or accelerometer as a sensor. In a preferred embodiment, it contains three magnetometers, arranged orthogonally.

The sensor unit of the invention is smaller in cross-section than the pipeline, and does not impede the flow of liquid in the pipeline. Instead, it travels with such flow. Thus, it does not create significant back pressure or impede the flow of liquid in the pipeline. Further, it can be made small enough to be used in pipelines which are too small for a human to enter, and in which inspection by a human is therefore not possible.

The sensor unit (which includes the sensors, associated equipment, and a battery within a protective external structure) is generally ball shaped. In one embodiment, it is spherical, giving it the shape of, for example, a tennis ball. In another form, it has one slightly elongated axis, giving it the shape of a ball as used in American or Canadian football or in English rugby (which shape will hereinafter be called "ellipsoid") Preferred forms of the sensor unit range from spherical (all axes equal) to an ellipsoid shape where one axis (herein called the "major axis" is up to about 30% longer than the other two, and the other two are equal.

In a preferred embodiment, the sensor unit has an incompressible inner package, preferably cylindrical or spherical, which contains one or more sensors, a recording medium and its power source (for example, a battery). This will be called the "sensor package" in this disclosure. The sensor package is contained within an outer ball-shaped unit, called herein the "ball". The sensor package and the ball unit together form the sensor unit of the invention.

In a preferred embodiment, the sensor unit is intended to roll along the bottom of the pipeline, as a ball rolls along the ground, with the motive force for its rolling motion given by the moving liquid in the pipeline. In order for the sensor unit to stay at the bottom of the pipeline, its overall density is greater than the density of the liquid with which the pipeline is filled.

In another embodiment, the sensor unit is provided with an overall density less than the liquid in the pipeline, and is intended to roll along the upper surface of the interior of the pipeline. In many pipelines, there are access ports arranged along the upper surface of the pipeline. Therefore, when this embodiment is used, the sensor unit should be sized so that it has a larger cross-section than any such valve or access port between the location where it is put in the pipeline and the location where it will be removed, to avoid it getting stuck.

In one preferred form, the sensor unit is spherical, like a tennis ball or soccer ball. If spherical, the diameter of the sensor unit is preferably less than half the diameter of the pipeline with which it is intended to be used. This permits it to pass under objects which bisect the pipe along a horizontal diameter, such as open butterfly valves. The diameter of the sensor unit should also be large enough so that the sensor unit can roll easily over small obstacles, such as a discontinuity in the wall of the pipeline where two pipe sections join, and so that the drag of the water will cause it to continue rolling onwards even when the pipe tilts uphill. The rolling action of the sensor unit adds angular momentum to the sensor unit. The angular momentum can assist in traversing obstacles such as bottom drains and make the ball less susceptible to entrapment by obstacles. Further, because the ball traverses the bottom center of the pipe, small outflows into adjoining pipes (which usually leave the pipe on a side rather than from the bottom) can be traversed without difficulty. In most cases, the diameter of the sensor unit should be greater than about $\frac{1}{10}$ of the pipeline diameter in order that it attracts sufficient angular momentum, but this depends somewhat on the nature of the obstacles and whether the pipe goes uphill in the direction of flow.

With these factors in mind, the preferred diameter of the spherical sensor unit is from about $\frac{1}{4}$ to about $\frac{1}{3}$ of the diameter of the pipeline in which it is to be used. However, for particular pipelines, spherical sensors outside this range are useable.

In another preferred form, the sensor unit is an ellipsoid with the major axis slightly longer than the two other axes at right angles to it, so that it has a form similar to a rugby ball or American football. If the sensor unit of this shape is dense enough relative to the liquid in the pipeline so that it rests on the bottom of the pipeline, it tends, when pushed by liquid flow in the pipeline, to roll along the bottom portion of the pipeline with its major axis perpendicular to the centre line of the pipeline. Similarly, if the density of the ellipsoid sensor unit is less than the density of the liquid in the pipeline, it tends to roll along the top of the interior of the pipeline with its major axis perpendicular to the centre line of the pipeline. This makes it unlikely that it will enter and become stuck in any access ports having a cross-section less than its major axis.

Generally, ellipsoid balls will preferably have their major axis less than half of the diameter of the pipeline in which they are to be used, and preferably between ⅓ and ¼ of the diameter of the pipeline. However, the use of sensor units with smaller or larger major axes may be suitable, depending on the nature of the pipeline.

In the preferred embodiment, the ball surrounding the sensor package is formed of an easily-compressible foam, such as low density open cell or reticulated polyurethane foam. Reticulated foam has no cell structure but only a matrix forming the foam. Reticulated foam is particularly preferred because it is less likely to retain air when immersed in the liquid flowing through the pipeline. A foam density of less than five pounds per cubic foot is suitable, but a density of less than one pound/cubic foot is preferred. The foam shields the sensor package from damage and gives the desired ball shape to the unit. It also creates less noise when rolling along the inside wall of the pipeline than the sensor package alone would do.

The foam of this embodiment can be compressed tightly around the sensor package for insertion into the pipeline, thus permitting insertion through an access port which is smaller than the sensor unit when expanded to its full spherical or ellipsoidal shape. Once it is within the pipeline, the foam decompresses and the sensor unit resumes its full size and shape. The shape when compressed can be approximately cylindrical, and of a diameter which permits it to be inserted by pushing it through a valve or inspection port which is smaller than the diameter of the fully expanded spherical or ellipsoidal shape of the sensor unit.

A plurality of balls of different external diameters, or some balls which are ellipsoidal and some which are spherical, can be provided with interiors sized to fit a standard size of sensor package. Sensor packages having different types of sensors (as hereinafter described) can also be provided. The sensor unit used in any pipeline, therefore, can be made to measure by choosing a suitable sensor package for the job to be done, and matching it with a ball of appropriate size for use in that pipeline to form an optimal sensor unit.

In an alternate embodiment, the ball is formed of ribs which bias outwardly to form a ball shape, and which are covered by a flexible plastic or fabric covering stretched into a ball shape by the ribs. In this embodiment, the liquid in the pipeline can enter inside the ball by passing through a liquid permeable fabric covering or by entering through suitable holes in an impermeable covering, so that the interior of the ball, except for the part occupied by the sensor package, is filled with the same liquid as is being carried in the pipeline. In this embodiment, the sensor package is preferably cylindrical.

The overall density of the sensor unit is chosen with regard to the density of the liquid being carried in the pipeline. The chosen density can be either less the density of the liquid in the pipeline or more than the liquid density, depending on the intended use. If the sensor unit is of a higher density than the liquid in the pipeline, the sensor unit will tend to roll along the lowest portion of the pipe sections making up the pipeline. If it is of a lower density than the liquid, and the pipeline is filled with liquid, the sensor unit roll along the upper portion of the pipe sections.

Thus, adjusting the density of the sensor unit permits the most detailed inspection to be either on the upper portion of the pipeline or the lower portion of the pipeline. It is also possible to inspect using more than one sensor unit. In such an inspection, one sensor unit can for example, be of lesser density than the liquid so as to collect data from the upper part of the pipe sections forming the pipeline, and one can be of greater density so as to collect data from the lower portion of the pipeline.

One way of reaching the desired density is including weights within the sensor package to reach the desired overall density, taking into account the density of the ball with which the sensor package is to be used. However, in most cases, it is preferred to have a sensor unit where the density can be varied easily depending on the particular use desired This can be accomplished easily when the ball unit is made of foam, by making a series of ball units of different density, and by placing the sensor package within the one of the series of ball units which will give an overall sensor unit of the density desired. It is also possible, although less preferred, to manufacture a ball unit and sensor package of materials which give an overall average density less than that of the liquid in the pipeline, and to provide within the ball or the sensor package suitable weights to bring the sensor ball to the desired density. Another less preferred way of providing variable density is to manufacture a ball unit which with its sensor package forms a sensor unit of greater density than the density of the liquid, and which has a removable portion which can be substituted with material of lesser density when desired.

One problem that can arise is that the amount of flotation that arises from the use of a foam ball changes with the pressure of the pipeline because any air remaining in the ball is compressed by that pressure. To remedy this, the foam ball is preferably exposed to a vacuum just prior to insertion into the pipeline to reducing the air pressure surrounding the ball to less than 0.1 bar and preferably to less than 0.001 bar. This removes virtually all of the air present and allows water to fully saturate the foam, particularly if the foam is reticulated foam. It also improves the acoustic transparency of the ball, allowing better detection of small acoustic signals by an acoustic sensor within the sensor package, because air trapped in the foam would serve to block some acoustic waves. Exposure to vacuum can be accomplished in a closed chamber just prior to insertion of the sensor unit into the pipe. The valve allowing the sensor unit to be inserted into the pipe can then be opened slowly to allow water to fill the chamber previously evacuated. This also offers an opportunity to sterilize the ball by introducing a sterilant into the same chamber. Sterilization of the ball can be a important consideration if the liquid in the pipeline is drinking water.

The sensor package according to the invention contains at least one sensor which can sense and record the number of revolutions of the sensor unit as it rolls along either the bottom or the top of the inside of the pipeline (By a "revolution" is meant the distance traveled by when one full circumference of the spherical unit rolls along the pipe, or the distance traveled by the ellipsoidal unit when it rolls sufficiently so that there is a full 360 degrees of rotation about the major axis. Sensing and recording revolutions can be done by any suitable instrument. For example, an accelerometer will sense each revolution as a repeat pattern of acceleration. Alternately, a magnetometer will sense the magnetic changes as its sensor approaches and retreats from the pipe wall during each revolution. When the sensor unit is ellipsoidal, a single instrument of this sort gives good results, although care should be taken so that it is oriented to sense in a direction other than exactly along the major axis. When the sensor unit is spherical, a single magnetometer or accelerometer may undercount revolutions slightly, as the axis of revolution of the sphere might fortuitously be aligned with the axis along which the instrument does not sense for short periods. It is therefore preferred to have at least two accelerometers or magnetometers oriented to sense in different angular directions (ie., which have an angular separation of other than 180 degrees in the direction that they sense), and to resolve the vector of their outputs when the sensor outputs are analyzed. It is particularly preferred to have three magnetometers or three accelerometers arranged orthogonally, and to count revolutions by resolving the vector of their individual outputs when the sensor outputs are analyzed. Typically the analysis is done by computer after the sensor unit has been removed from the pipeline and the data has been downloaded to a computer. An arrangement of three orthogonal magnetometers is shown in Canadian patent application 2,273,979 of Paulson.

The sensor package can in addition contain any suitable sensors for examining pipelines. For example, in one embodiment, the sensor package contains an acoustic sensor, such as a hydrophone, or a pressure sensitive sensor, such as a piezoelectric device, or other acoustic or pressure sensor.

For particular sensing requirements, any other suitable type of sensor can be used to meet the particular requirement. For example, temperature sensors can be used where it is desired to get a temperature profile of liquid temperature along the length of a pipeline. Chemical detectors can be used where it is desired to find the location where a chemical contaminant is entering a pipeline.

The sensor package also contains means for preserving the readings of the sensors. Generally, this will be a recording device, preferably a digital memory. The preferred storage medium is a removable memory device such as an SD-Ram card.

The sensor package also contains suitable power supply means to supply power to those sensors that require it and to the recording device. Most conveniently, this is a long-life battery. A non-rechargeable lithium battery is currently preferred on the basis of cost, performance and size, but it is possible to use any other battery or other power supply with delivers a suitable voltage to power the sensors and the recording device, and which can store enough energy to power these for the intended period of use.

In one embodiment, the sensor package records data, and the data is recovered when the sensor unit is retrieved at a downstream point, and is then analyzed by a suitable computer Anomalies found by any of the sensors (such as a leak found by the acoustic sensor, or corrosion found by the magnetic sensors) can have their locations along the pipeline determined by noting the number of revolutions of the sensor unit which had occurred when the anomaly was sensed. Because the circumference of the ball is known, the rate and distance of travel are also known by counting the revolutions and multiplying the revolutions by the circumference of the ball. Magnetometers are preferred over accelerometers, as the magnetometers also record passage over pipe joints and passage near other features of the pipeline, such as side passages, which help to verify the location.

Other means may also be used to verify the locations. If the speed of liquid flow along the pipeline is known (as for example by pumping station records or stationary flow sensors in the pipeline) and is relatively constant, the location associated with the data being collected can be estimated from the elapsed time between the time the sensor unit was released into the pipeline to move with the liquid flow and the time of the acquisition of the data of interest. If the data is recorded as a real time recording, no clock is necessary, although a clock trace can be provided with the data collected if desired. If data is compressed, it is preferred to have a clock trace recorded with the data.

In another embodiment, acoustic markers are placed at known locations along the pipeline and a sensor package which records acoustic data is used. The recording of signals from these markers by the acoustic or piezoelectric sensor in the sensor package gives a good indication of the speed at which the ball is travelling in the pipeline, and the point in the data recording at which the sensor passes each marker. The location from which the data of interest was collected can then be interpolated between known locations such as the location where the ball was placed in the pipeline, the locations of the markers, and the location where the ball was removed from the pipeline. Preferably, each acoustic marker has a different signal, so that it is easy to distinguish the signals of the markers from one another. The points in the record of the acoustic sensor at which the sensor passes the location markers can be noted, and the particular location at which an anomalous signal has been received can be determined by noting the location marker past most recently before the anomalous signal, and the next location marker passed after the signal, and prorating the continuous signal to determine the location, by assuming that the speed of the sensor unit between the two location markers is constant. To verify whether the speed was or was not constant, reference can be made to the distance traveled according to the number if revolutions.

Another way of determining the location of the sensor in the pipeline is by providing the sensor unit with a magnetic sensor, preferably sensitive on more than one axis, and recording the signal from such magnetic sensor. In metal pipelines, the pipeline sections are joined by welds, which will provide a magnetic anomaly which can be noted by the magnetic sensor when the sensor unit passes over a welded joint. In concrete pipelines, there is a bell and spigot arrangement at the end of each section, where a portion of one pipe (the bell) overlaps for a short distance on another pipe (the spigot). Since concrete pipes are reinforced by wire wrapping within the concrete, the joints will have two overlying sets of wire wrappings, one from each pipe, and also a steel bell and spigot detail that exists only at the joints, and which will also provide a magnetic anomaly. Thus, a person plotting the location of an acoustic anomaly can consult the records of the pipeline construction, to find out where the joints are, and correlate the number of joints crossed (by the magnetic anomalies that are exhibited when a joint is crossed) against any other anomaly sensed by any sensor in the sensor package. Thus, if an acoustic sensor is present and detects an acoustical anomaly, such as a leak, correlation with the results from the magnetic sensor permits the location of a leak to be identified to within one pipe length. By assuming constant speed along that pipe length, one can pro-rate the time taken to traverse that pipe length, and find the leak location with very great accuracy.

A magnetic sensor can also acquire other useful information. In a concrete pipe, for example, if the wires wrapping the pipe have been severely corroded or damaged, this can create a magnetic anomaly at a location which is not a joint between pipeline sections. In a welded metal pipeline, if the weld has begun to fail, the magnetic signature can be different from the signature of welds which are intact. Thus, the magnetic sensor can also provide useful information about the state of the pipe, as well as providing a location function for any acoustic anomalies.

In an embodiment where the sensor package contains a magnetic sensor, magnetic or electric transponders having distinctive signals can be located at known locations along the pipeline. These will record in the magnetic recording which is made as the sensor unit passes their locations In a particularly preferred embodiment, there are three magnetic sensors, arranged orthogonally. Thus, where an unanticipated magnetic anomaly occurs, for example, one which is not a normal magnetic anomaly encountered at a pipe joint, the three orthogonal magnetic sensors will record the magnetic anomaly differently, If the orientation of the three orthogonal sensors is known (as, for example, by locating them relative to the down direction as shown in C.P. A. 2,273,979 of Paulson), then the location around the circumference of the pipeline from which the magnetic anomaly is being recorded can be determined. This assists in locating the anomaly for the purpose of subsequent inspection of another nature, as for example by a tethered video camera.

Where there are several possible pathways for the sensor unit, the path can be manipulated by selectively opening and closing valves to direct the flow of liquid in such a way as to take the sensor unit into pipes where inspection is needed.

In another embodiment, the sensor unit or the ball can contain an acoustic transmitter or transponder, signals from which can be picked up by receivers or other transponders at intervals along the pipeline (such as at inspection ports). This permits a remote operator to keep track of the progress of the sensor unit. These transponders emit frequencies higher than the audible range, preferably frequencies above 20 KHz. because higher frequencies tend to propagate very long distances in a pipe. The use of transponders transmitting at more than one frequency or as a sweep of frequencies over a range can allow an estimate of the proximity of the sensor unit to a surface detector, because the lower frequencies would attenuate more rapidly with distance. The ratios between the amplitude of the signals at different frequencies can therefore provide an indication of proximity and therefore, over time, the direction of motion whether toward or away from the detector. A preferred range for such a swept pulse is be between 1 KHz. and 200 KHz.

The sensor unit is preferably inserted into the pipeline in collapsed form. If the ball is foam, it is compressed about the sensor package. The sensor package is preferably spherical, and small enough so that it, with the ball squeezed about it, can be pushed through an inspection port or valve. For example, for many applications it is preferred to have a sensor unit which can be compressed so it can be pushed through a 4 inch (10 cm) diameter inspection port. Once inside the pipeline, the foam expands to the full intended diameter of the sensor unit, so that the sensor unit has a larger resistance to water flow, making it easier for the water to push it up inclines.

To permit collapse of the foam, the foam ball may have cores removed to form small circular or conical holes in it, for example of 1 to 4 centimeters in diameter each. This reduces the amount of foam that needs to be compressed, but still preserves the full diameter of the sensor unit.

If the ball is an embodiment which has expandable ribs, it is pushed into the pipeline by an actuator, and further pressure is applied to the actuator to expand the ribs so they spring into a spherical shape.

For full inspection, it may be desired to release several sensor units within a short space of time. One, for example, can have a density such that it will roll along the bottom of the pipeline. A second can, for example, be of lesser density than the pipeline, so that it will roll along the top inside of the pipeline. A sensor unit of lesser density than the liquid in the pipeline should not be used if there are any manholes or other access ports into which it might rise and be entrapped before it travels the distance intended for inspection, or downward projections from the roof of the pipeline (such as a valve structure) which it might not be able to pass.

Another occasion on which several sensor units can be used is when a first sensor unit has detected a leak, and the position of the leak has been plotted by the number of revolutions through which the sensor unit had traveled. Then, surface acoustic transponders or vibrators can be placed on the surface near the estimated position of the leak. A second sensor unit is then released, and the location of the leak and the location of the transponders or vibrators are noted from the recording it makes. This allows the comparison of the leak position with the positions of the surface transponders or vibrators, allowing very accurate estimation of leak positions. In this case, the use of low frequency acoustic vibrators is, preferred because the signals can penetrate through the ground cover and the pipe wall.

After the desired inspection distance has been traversed, means are provided for retrieving the sensor unit. In a simple embodiment, an inspection port is opened as the sensor unit approaches it, venting pipeline liquid (which is at a higher pressure than atmospheric) to the atmosphere. This entrains the sensor unit in the liquid escaping from the pipeline and ejects it.

More preferably, however, a ball catching apparatus is disposed. A preferred ball catching apparatus for a foam ball sensor unit is a pipe which is inserted into the pipeline through a valve or inspection port. The inserted pipe is equipped with a net which deploys to direct the sensor unit toward a hole in the inserted pipe. Initially, the pressure in the inserted pipe is the same as that in the pipeline. When the ball is adjacent the hole, the pressure in the inserted pipe is reduced, for example by exposing the other end of the inserted pipe into atmosphere. The ball is sucked into the hole by the difference in pressure between the pressure in the pipeline and the lower pressure inside the inserted pipe. The foam compresses to pass through the hole into the pipe, so that the ball is squeezed through the hole and passes thorough the inserted pipe, out of the pipeline. The pipe is then withdrawn from the pipeline, collapsing the net as it goes.

Another embodiment of a sensor unit catching device, useable either with a sensor unit having a foam ball or a sensor unit having a fabric cover and supporting ribs is a net lowered through a manhole or valve opening to block the passage of objects through at least part of the pipeline, while permitting liquid to pass. As the sensor unit is known to be rolling along the bottom of the pipeline (if more dense than the liquid) or rolling along the top of the pipeline (if less dense than the liquid), it is usually only necessary to block only the bottom (or top, as the case may be) with the net. The sensor unit is then retained by the net. The sensor unit can then be retrieved by manipulating the net to envelop the sensor unit, then removing the net through the manhole.

Once the sensor unit is retrieved, the recordings made by the sensors are read Acoustic, magnetic, temperature and/or chemical anomalies are noted (depending on what sensors were present) with respect to their location along the pipeline. Further examination, using another type of sensor can then be carried out at those locations, or the exterior of the pipeline at those locations can be accessed for necessary repair work.

BRIEF DESCRIPTION OF THE DRAWINGS

The invention will be described further with respect to the drawings, in which.

The drawings are schematic and not to scale.

DETAILED DESCRIPTION OF THE INVENTION

Figure 1:
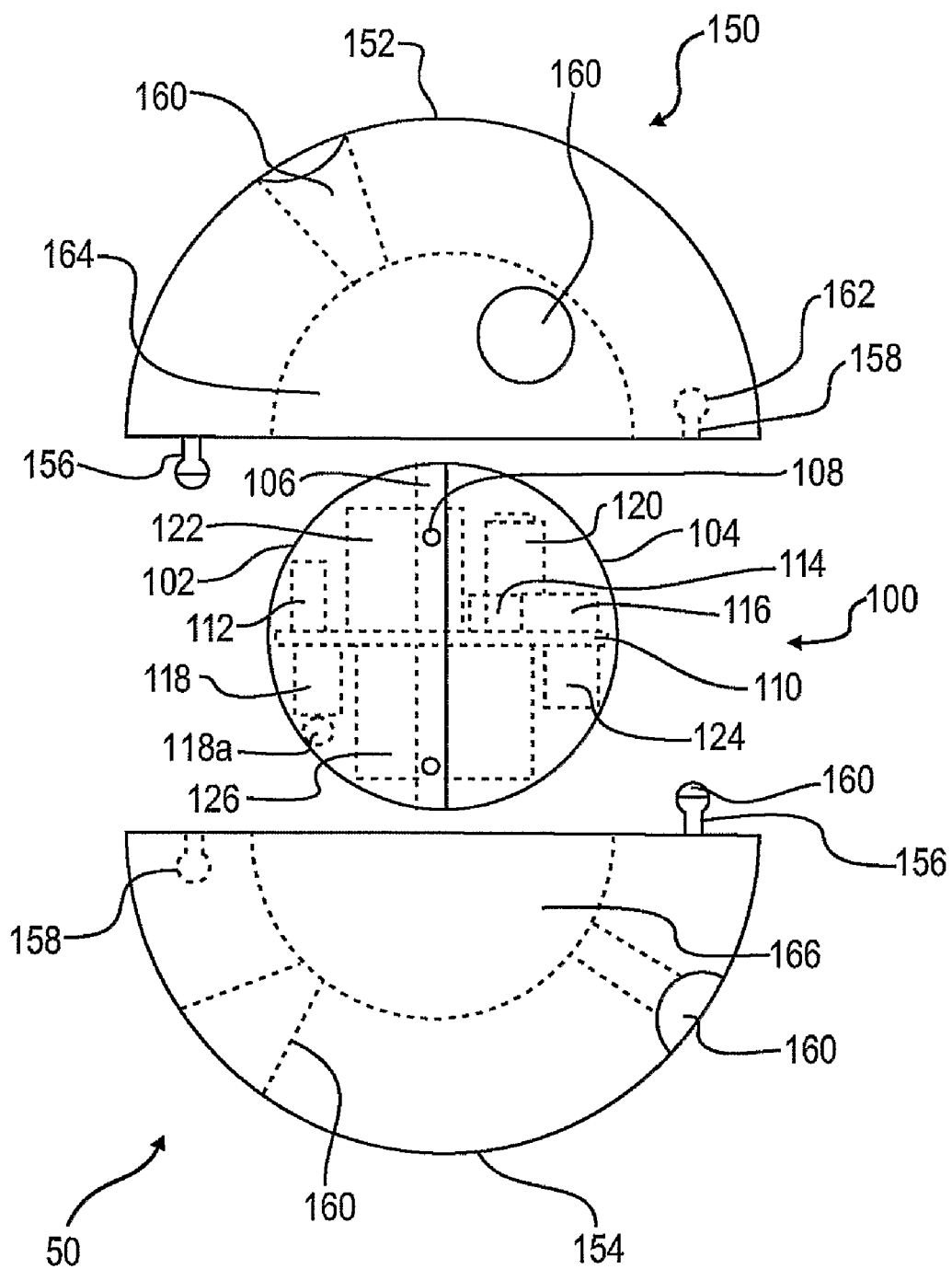
FIG. 1 shows one preferred type of detector unit according to the invention, which has a spherical foam exterior.

FIG. 1 illustrates one preferred embodiment of the sensor unit according to the invention, shown in partly disassembled form. The partially disassembled sensor unit (sensor package plus ball unit) is shown diagrammatically as 50. A sensor package 100 is made of some rigid material, such as a rigid plastic. The sensor package can also be of metal or other material, if the sensors to be disposed within it are such that a metal package would not affect their sensitivity to external stimulus.

In the embodiment shown, the sensor package has two half shells 102 and 104. Half shell 104 has a lip 106 which fits under half shell 102 and is held in position by screws 108. Obviously, other means for closing the sensor package and retaining it closed can be used.

Within the sensor package is a circuit board 110. This is provided with suitable circuitry to connect the sensors, power source, recording device, clock and any other components of the sensor package. Obviously, separate connections could be used rather than a circuit board, but this is cumbersome and not preferred.

Mounted on circuit board are one or more sensors shown schematically as 112, 114, 116 and 118. For example, there can be an acoustic sensor, one or more magnetometers and/or one or more pressure sensing devices, or temperature recording devices. If magnetometers are present, it is preferred to have three magnetometers oriented orthogonally to one another. This is indicated schematically in FIG. 1 where sensors 112, 114 and 116 are magnetometers orthogonal to one another. Sensor 118 is an acoustic or pressure sensor, for example a microphone or hydrophone, or piezoelectric sensor. Sensor 118 has its acoustic sensing portion 118a in acoustic contact with the wall of sensor package 100, to get good passage of acoustic signals through the wall.

Also mounted on the circuit board is a recording device 120, which records to a removable memory 122. Suitably, the recording device is a simple digital recorder, which receives (and converts to digital if necessary) the sensor outputs and records them to the memory. The preferred memory is an SD Ram card.

Optionally also a clock 124, which records a clock trace on the memory 122, is also mounted on circuit board.

The circuit board 110 also has mounted on it power source 126. Conveniently, this can be a non-rechargeable battery, such as a lithium battery. However, rechargeable batteries or any other self-contained energy source of a suitable size can be used.

A foam ball unit 150 is provided. It is shown disassembled in FIG. 1. It is made preferably of compressible foam, for example soft polyurethane. Reticulated low density polyurethane foam is preferred. It is provided as two half spherical pieces, 152 and 154, which can be joined to one another by engaging hard plastic prongs 156 in recesses 158. Prongs 158 have enlarged heads 160 which fit into enlarged ends 162 of the recesses to retain half spheres 152 and 154 together in use. Pieces 152 and 154 have a hollow portions 164 and 166 respectively which are just large enough for sensor unit 100 to fit within when the pieces 152 and 154 are assembled to form foam ball unit 150. The pieces 252 and 154 have passing though them circular or conical holes 160, whose purpose is to reduce the amount of foam which has to be compressed when the unit is compressed to be placed in the pipeline. Preferably one of the holes is also located so that the portion of the wall of sensor package 100 where acoustic sensor 118a is located is not covered by foam, to ensure a good acoustic signal. preferably, also, the holes are spaced fairly evenly over the surface of the pieces 252 and 354, so as not to impeded the protective function of the foam and not to unbalance the weight of the entire unit.

Figure 2:
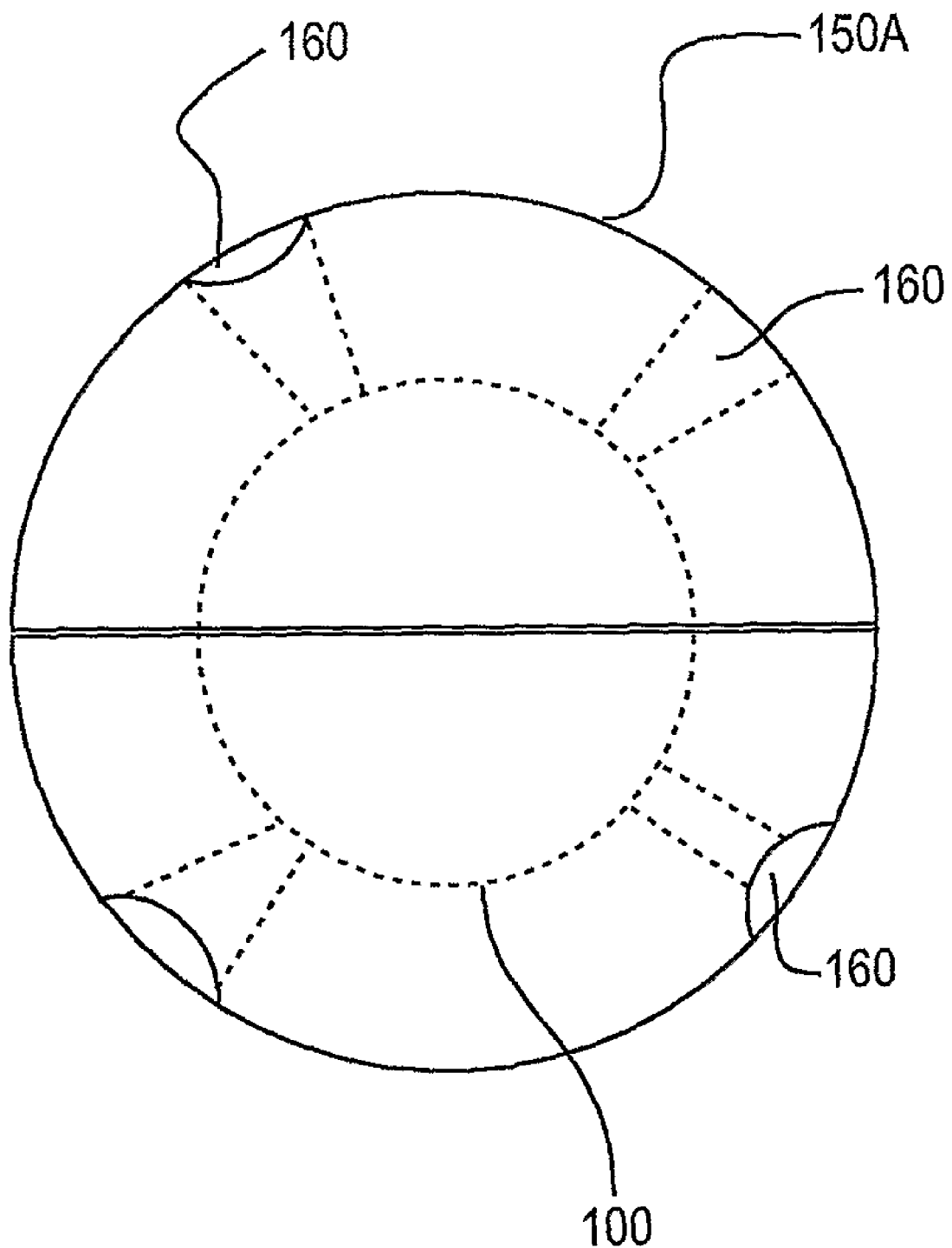
FIG. 2 shows a variant of FIG. 1, in which the foam exterior is ellipsoid.

FIG. 2 shows a variant of FIG. 1. The sensor unit 100 is the same as that of FIG. 1. However the foam ball unit (numbered 150A and shown assembled, is ellipsoidal (shaped like a rugby or North American football ball.)

Figure 3:
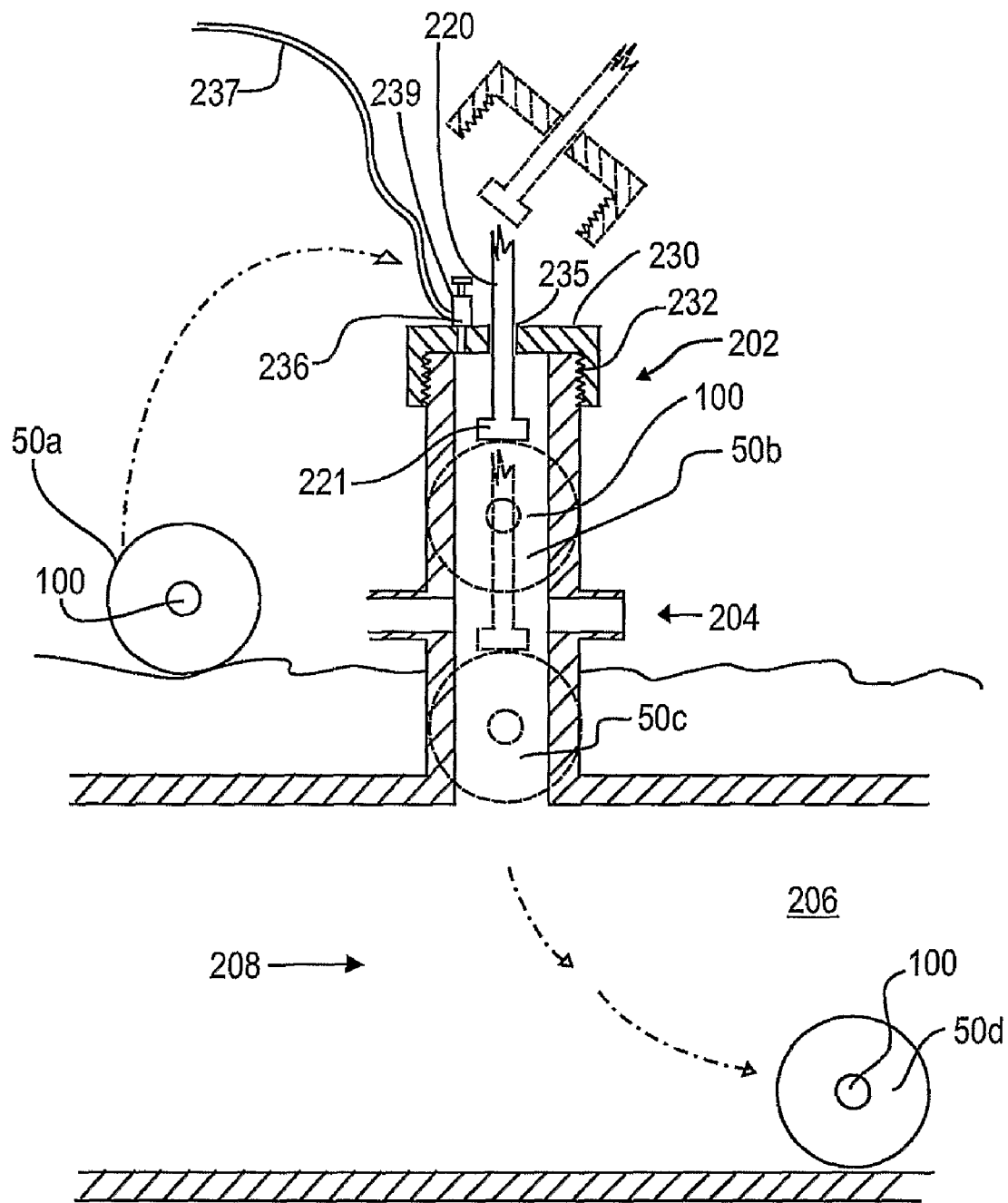
FIG. 3 shows a sequence of steps for insertion of a foam covered sensor unit into a pipeline, the pipeline being shown in cross-section.

FIG. 3 shows the insertion of a sensor unit 50 (after being fully assembled by joining together pieces 152 and 154) into a pipeline 200 filled with liquid 206 (for example water) flowing in direction 208. There is an access port 202 (also known as an inspection port) in the top of the pipeline. This is normally closed by a valve shown schematically as 204. In the figure the valve is closed At the top of the access port 202 is a screw thread 232. Initially nothing is mounted on this screw thread. A sensor unit (shown initially in position 50a) is brought to the site It is then squeezed into the position shown as 50b. A cover 230 is then screwed in pressure-tight fashion on the thread 232. The cover has a pressure tight gland 235 through which passes a rod 220, terminating in a pusher 221, which is suitably plastic or metal. It also has a small bore 236 to which a suitable value 239 is fastened. A line 237 can be connected to the valve.

The sensor unit is shown in four sequential positions, 50a, 50b and 50c. and 50d. In position 50a, it is resting on the ground surface 210, prior to insertion. In position 50b, the valve 204 has been opened and the foam unit has been compressed to squeeze through the access port 202 above valve 204. Then, the cover 230 is put on. When cover 230 has been secured in pressure tight relation, optionally a vacuum is created in the space between cover 230 and valve 204 by withdrawing air through valve 139 and line 137, to remove air entrained in the foam of ball 50. A sterilizant can also be introduced through line 237 and valve 239 if thought desirable. Valve 239 is closed and valve 204 is then opened, so that liquid from the pipeline enters the space between valve 204 and cover 230. When the space between valve 204 and cover 230 is full of water, rod 220 is pushed manually, to force the sensor unit first into position 50c and then into the pipeline as at 50d, where it recovers its full size.

Figure 4:
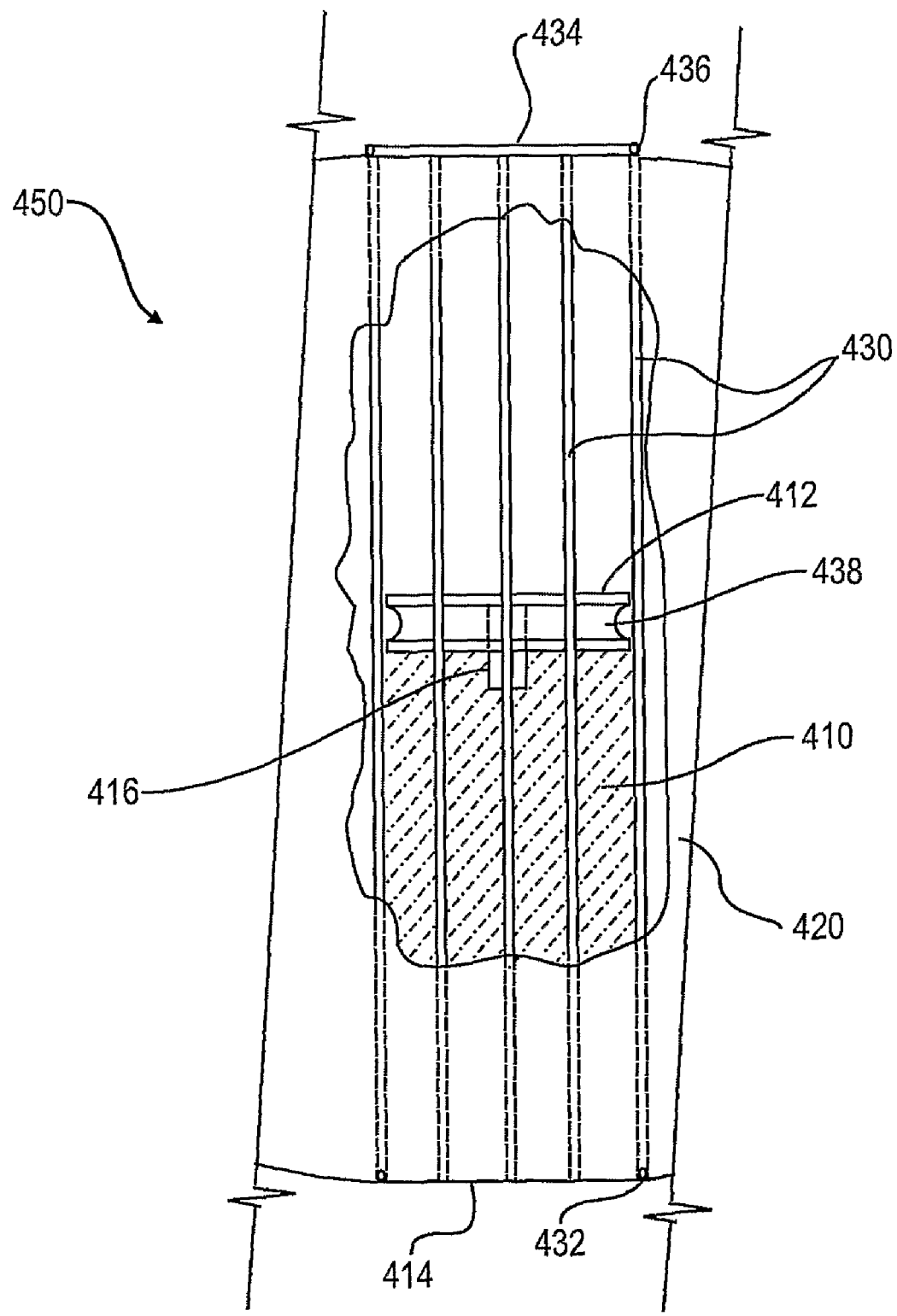
FIG. 4 shows a further embodiment of the sensor unit, having ribs and a fabric exterior, in collapsed form.
Figure 5:
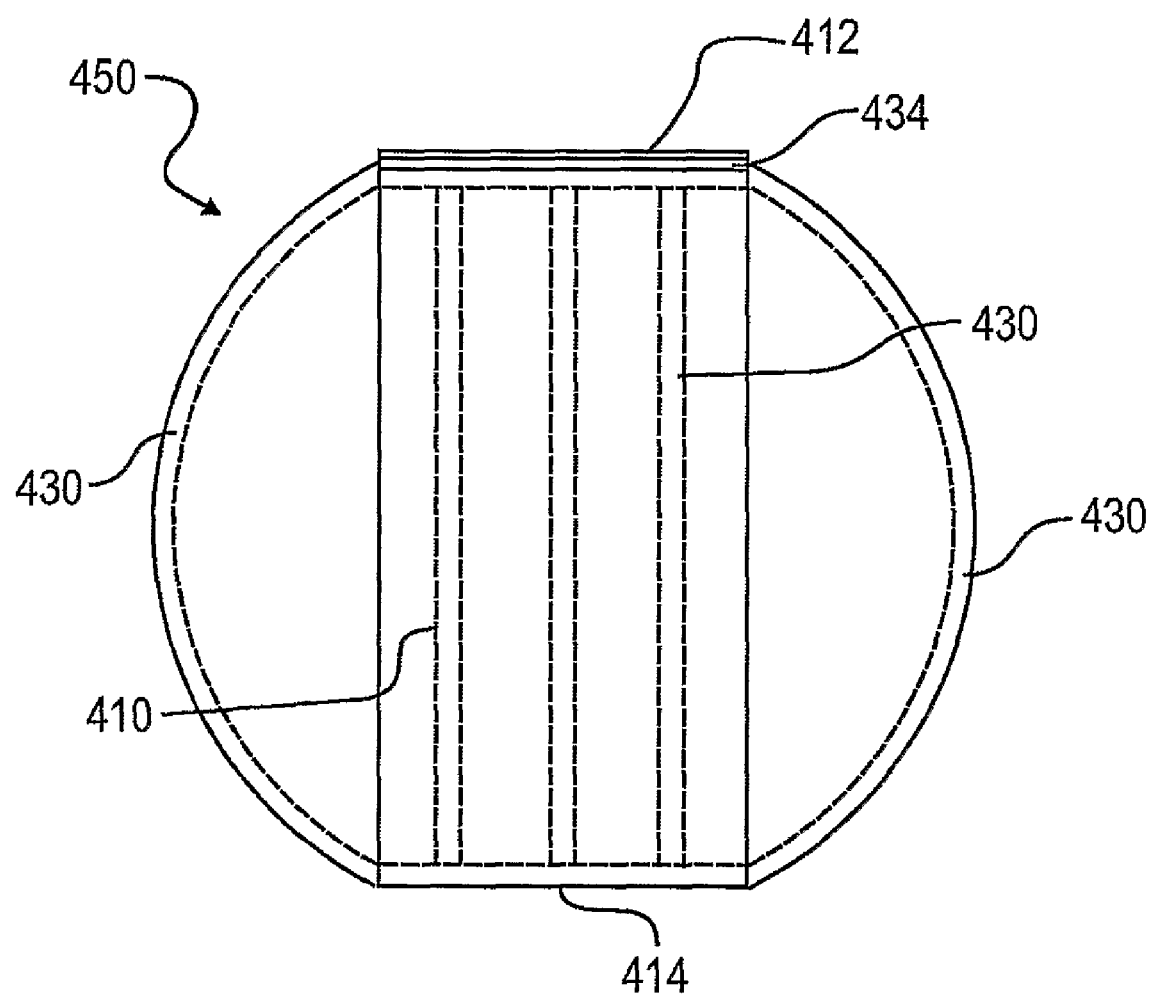
FIG. 5 shows the sensor unit of FIG. 4, in expanded form.

FIGS. 4-6 show a second embodiment of the sensor unit. This embodiment is generally numbered 450. It has a cylindrical sensor package 410, and a fabric exterior 420. The sensor package contains the same sensors and other components (not shown) as sensor package 100 of FIG. 1. Ribs 430 are flexibly attached to one end of sensor package 410 at 432, and terminate at the other end in a flexible connection 436 to a ring 434 which is stretchable. Package 410 has a recess 438 into which the ring 434 can lock, as will be shown, and two flat ends 412 and 414. End 412 has a recess 416 into which an insertion tool can fit. Ribs 430 support fabric 420, which will form the ball shape.

In FIG. 4, the sensor unit 450 is disassembled for insertion into a pipeline. The ribs extend upwards beyond the end of the sensor package 410, with the fabric 440 overlaying them. The fabric has been cut away to show the ribs. In FIG. 5, the sensor unit is fully assembled. Ring 434 is locked into position in recess 438 and the fabric, pushed by the ribs, has assumed a ball shape with flattened ends 412, 414 at the end of the sensor package 420.

Figure 6A:
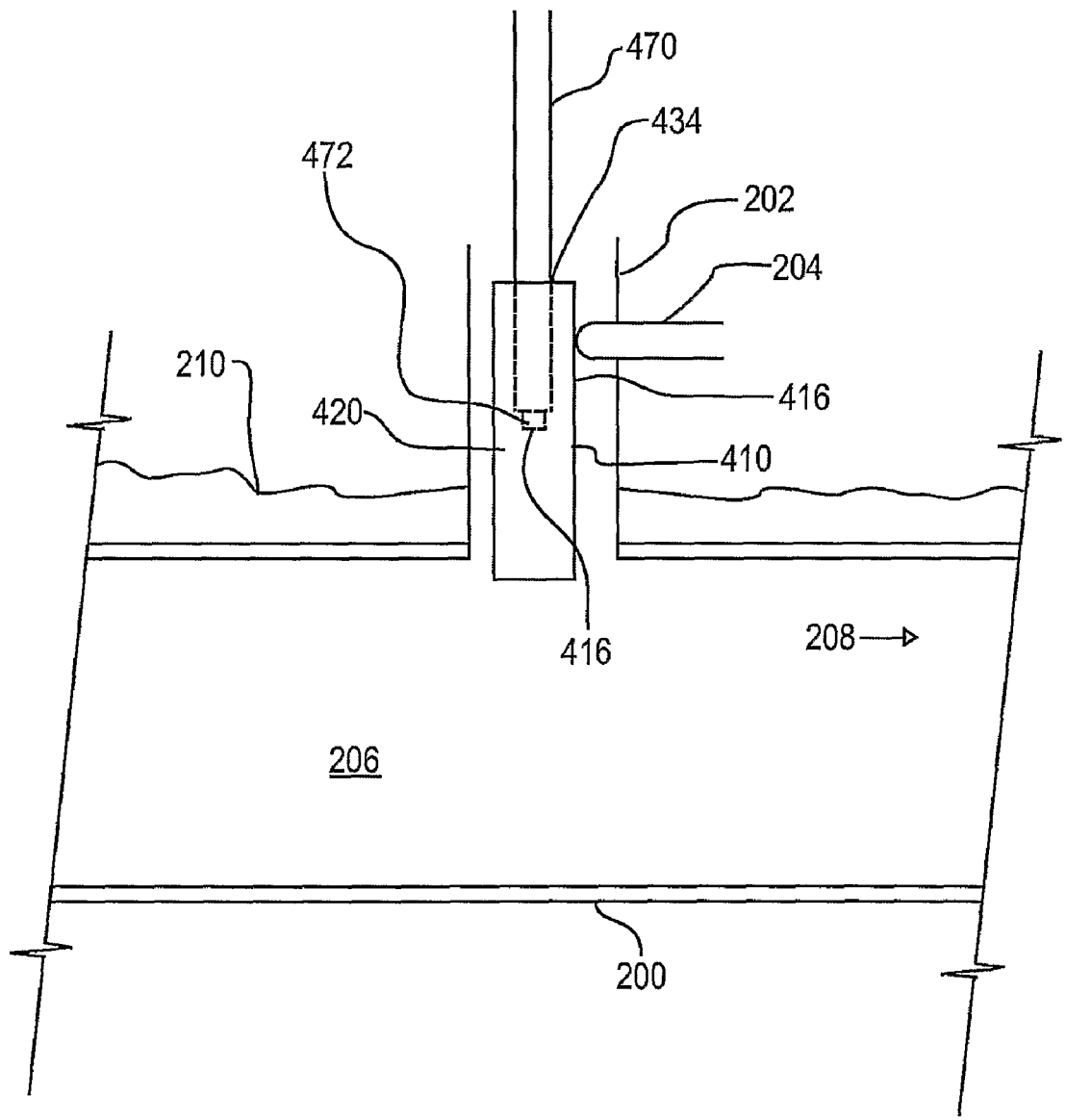
FIGS. 6a and 6b show the insertion of the embodiment of FIG. 4 into a pipeline.
Figure 6B:
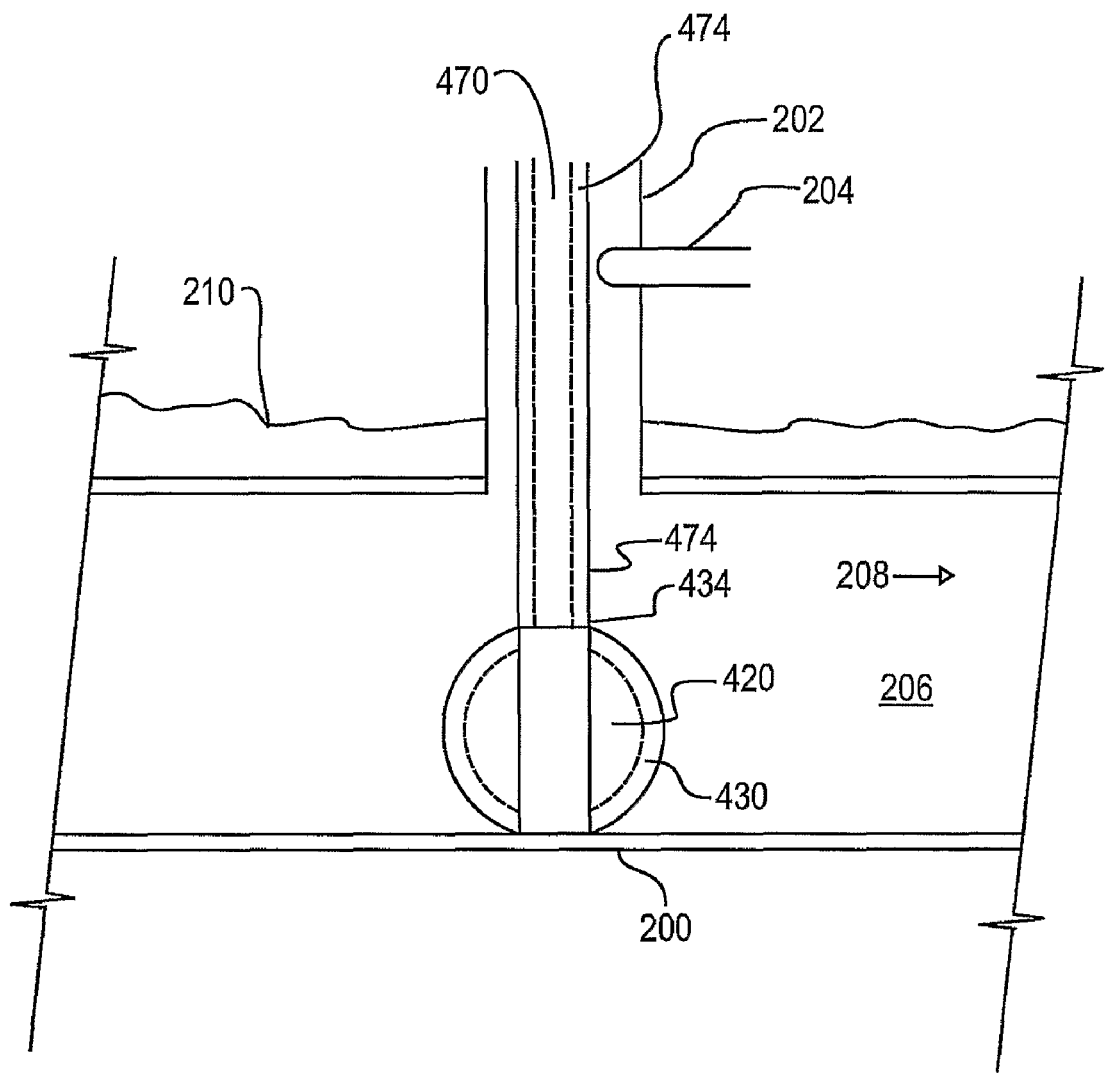

FIGS. 6a and 6b show the sequence of insertion of the sensor unit 450 into the pipeline and its final assembly within the pipeline. The pipeline is the same as in FIG. 3, and the same numerals will be used to describe it as in FIG. 3. The sensor unit 450 is releasably attached to the end of an insertion device 470, as by a loose compression fit of a rubber bottom end 472 of insertion device 470 in recess 416. The insertion device is then lowered through the valve 204 into the pipeline. The diameter of cylindrical sensor package 410 is sufficiently small to pass through the access port 202 and past valve 204. In FIG. 6a, it is in the process of passing valve 204. In FIG. 6b it is within the pipeline. A sleeve 474 is lowered on insertion device 470 to push ring 434. It pushes until ring 434 snaps into recess 438, at the same time bending the ribs to force the fabric into a ball shape. The interior of the ball is filled with the liquid of the pipeline. The fabric can be permeable to the liquid, or can be provided with holes (not shown) to permit the liquid to enter. The sleeve 474 is then left in position while insertion tool 470 is removed from recess 416. Insertion tool 470 and sleeve 474 are then withdrawn through access port 202 and valve 204 is closed.

Figure 7:
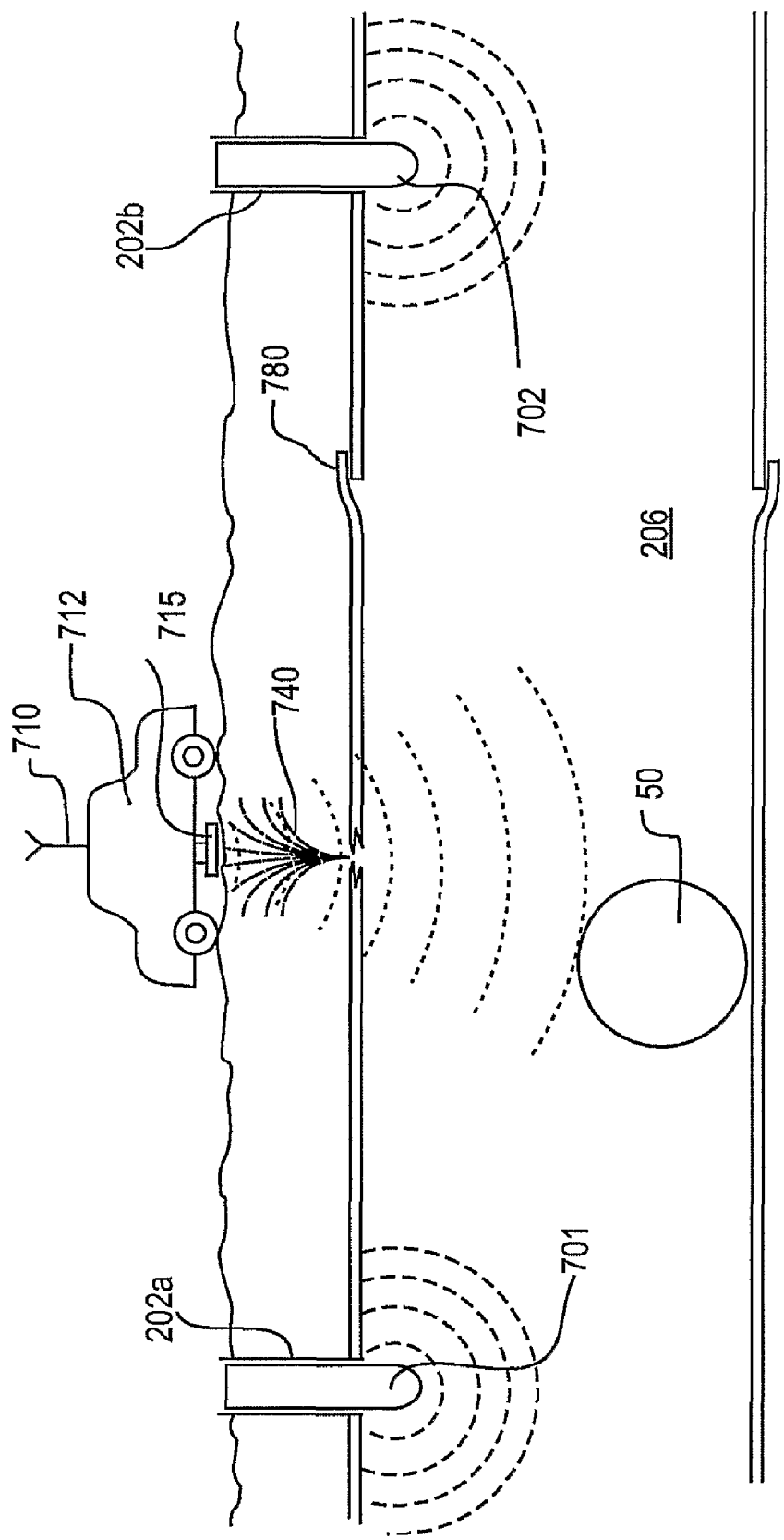
FIG. 7 shows passage of a sensor unit along the bottom of a pipeline.

FIG. 7 shows a sensor unit 50 moving through the pipeline. In the embodiment shown, the sensor unit is more dense than the liquid in the pipeline, so the sensor unit rolls along the bottom of the pipeline. It passes acoustic beacons 701, 702 placed in access ports 202a and 202b respectively. The signals from these beacons are received by the acoustic sensor 118 in sensor unit 50. If it is suspected that a leak is in the area (because for example a previous sensor unit has detected one), a mobile acoustic beacon 715 (shown here positioned on a vehicle 712) can be positioned on the surface near the expected leak. Mobile beacon 715 transmits at very low frequencies (below about 1000 Hz) so that its signal will not be attenuated by the earth and the walls of the pipeline. Mobile beacon 715 is also provided with a GPS transmitter/receiver 710 so that its position will be known exactly. The signals from the beacons are recorded by the acoustic sensor, or they are recorded by recording device 122 to provide a reference to the location of the sensor unit when the recording is made.

There is a leak 740 in the pipeline, and the escaping liquid gives a characteristic sound which is detected by the acoustic sensor and recorded with the other signals of that sensor. Subsequent analysis can determine the location of the leak, either by comparison with the signals recorded from the beacons or by reading the clock trace to see the elapsed time since the sensor unit was released, and knowing the speed of liquid in the pipeline, or by the counting of the revolutions of the sensor unit.

The pipeline is a concrete pipeline wrapped with wire. The magnetometer sensors in sensor unit 50 register increased signals when the sensor unit 50 passes a bell and spigot joint between two pipes as at 780, as there are more wires at the joint than in the pipe and because there is a metal insert at that location. The magnetometer sensors also note magnetic anomalies if there is corrosion in the wires, and these are recorded on the recording medium or transmitted, or both. The location can be determined by elapsed time or by correlation with the acoustic record which is left by the acoustic beacons on the recording medium or which is transmitted.

Figure 8A:
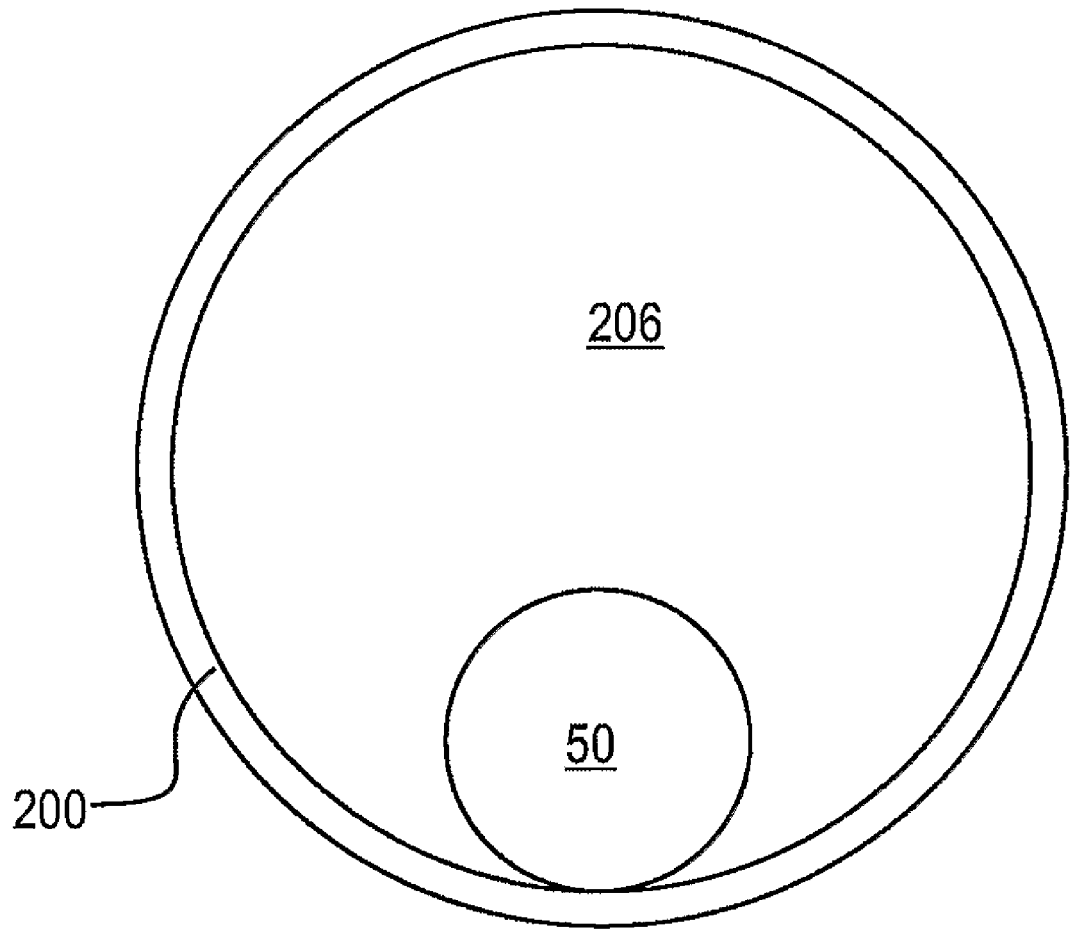
FIG. 8A and FIG. 8B show a cross-section of the pipeline of FIG. 7, showing how the sensor unit (a spherical sensor unit in FIG. 8A and an ellipsoidal sensor unit in FIG. 8B) move along the bottom of the pipeline.
Figure 8B:
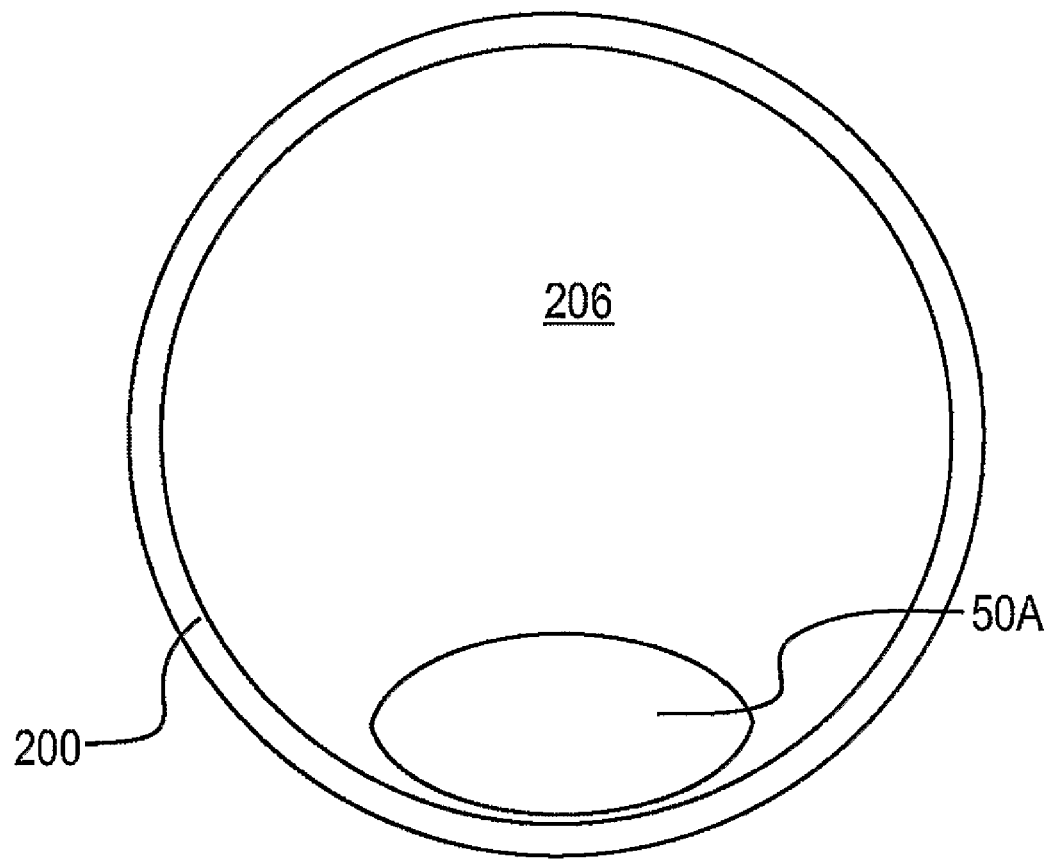

FIG. 8A shows a cross section through pipeline 200, showing how sensor unit 50 rolls along the bottom of the pipeline. FIG. 8B shows the position that an ellipsoidal sensor takes up, with its larger axis at right angles to the axis of the pipeline.

Figure 9:
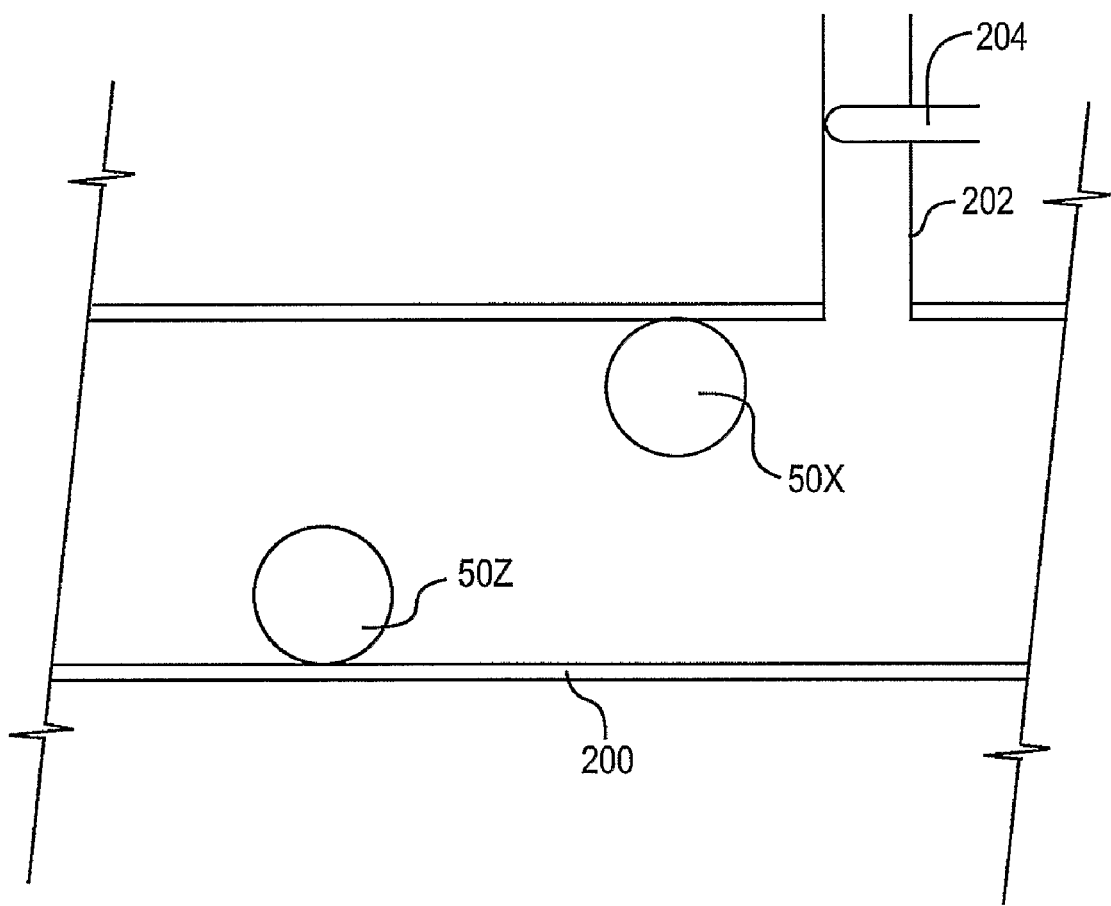
FIG. 9 shows two sensor units of two different densities disposed in a pipeline.

FIG. 9 shows two sensor units of different density, and how they move through the pipeline. Sensor unit 50x is of lesser average density than the pipeline, and is used only when the pipeline ifs filled with liquid. In the embodiment shown, the pipeline is filled with liquid, so it rolls along the roof of the pipeline. It is larger in diameter than the inspection ports encountered on route, so does not get lodged in such inspection ports. Sensor unit 50z is of greater average density than the liquid in the pipeline, so rolls along the bottom. The sensor units are shown as being of different diameters, but can be of the same diameter if desired.

Figure 10:
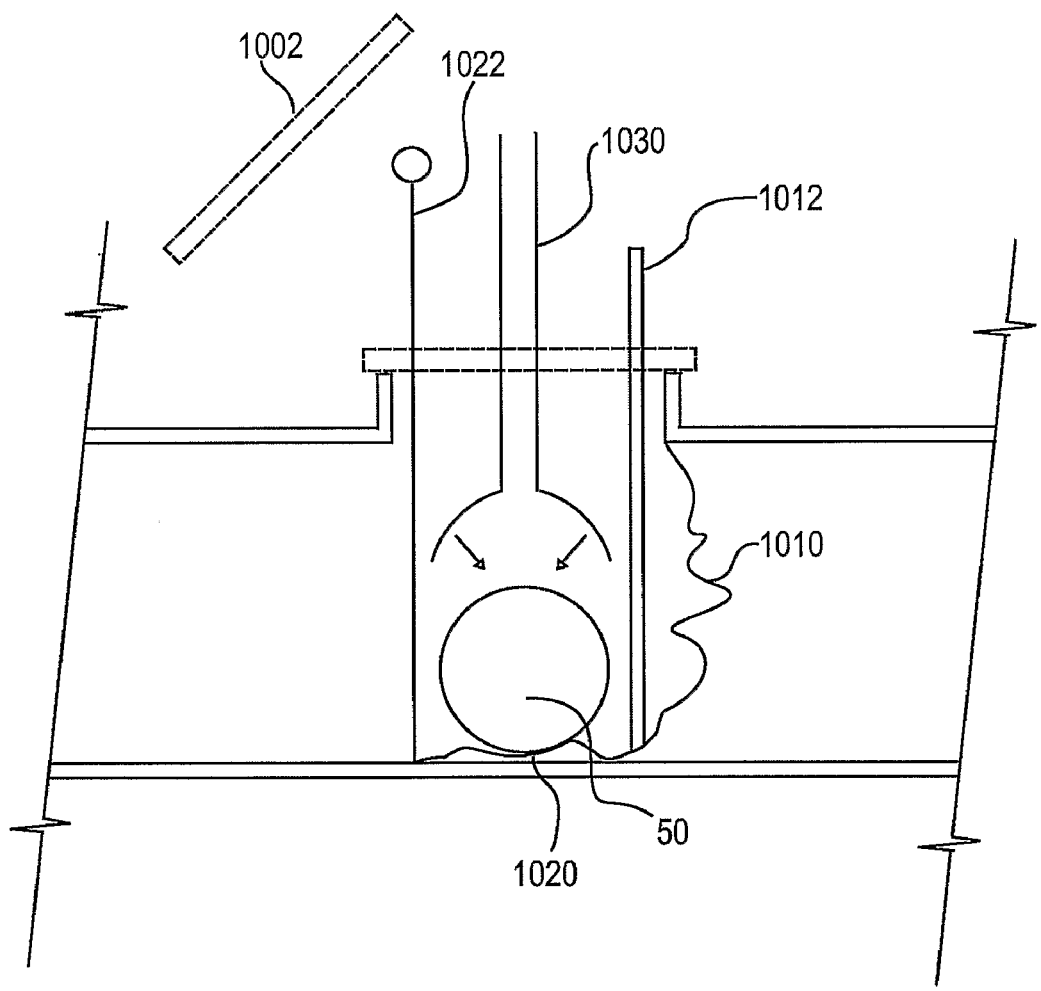
FIG. 10 shows one method of removing a sensor unit from a pipeline, by inserting a net.
Figure 11:
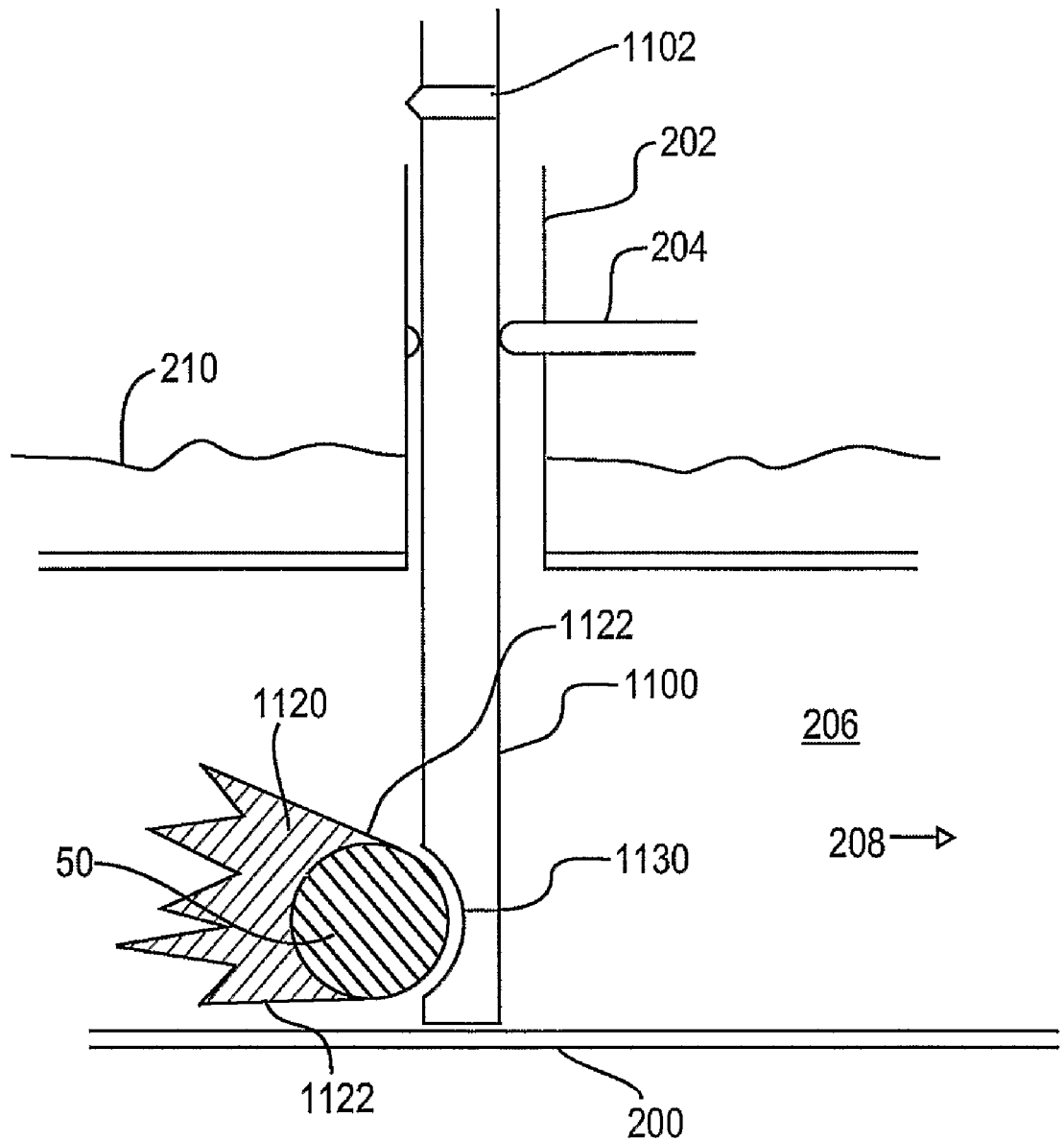
FIG. 11 shows a preferred method of removing a sensor unit from a pipeline which is pressurized, by using an inserted recovery pipe.

FIG. 10 shows one means for removing a sensor from a pipeline, when inspection is finished. This is useful in a pipeline which is at atmospheric pressure. A manhole 1000 has been opened by removing manhole cover 1002. and a net 1010 has been positioned to block the pipeline using positioning poles 1012. A further portion 1020 of the net, with lifting straps 1022, is positioned on the floor of the pipeline. The sensor unit 50 rolls along the floor of the pipeline (the sensor unit in this embodiment being of greater density than the liquid in the pipeline, until it hits net 1010, which prevents it from moving further. It is then on the portion 1020. Poles 1012 and lifting straps 1022 are operated to pull the sensor unit from the pipeline. Instead of using net portion 1020 to engage the sensor unit, alternatively one can engage it manually with claw-type grapple 1030.

Where the liquid in the pipeline is under pressure and the sensor unit is has a spherical compressible ball outer surface 150, the method of sensor unit retrieval shown in FIG. 11 is preferably used. FIG. 11 shows a recovery pipe 1100 inserted through an inspection port (also known as an access port) 202, with the valve 204 closed tightly around the pipe. Recovery pipe 1100 has its own valve 1102, which is also closed so that pressure does not escape from the pipe. Recovery pipe 1100 has attached to it a cone shaped net 1120, which is deployed by resilient ribs 1122, which are compressed during insertion of the recovery pipe into the inspection port, but then expand to deploy the net. The net causes the sensor unit 50 to drift to the apex of the cone. At the apex of the cone is a hole 1130 in the inspection pipe. The hole is slightly smaller than the diameter of the ball unit. When the ball is in the cone, the recovery pipe valve 1102 is opened quickly to atmosphere. As the atmospheric pressure is less than the pressure in the pipe, the sensor unit is slightly compressed and sucked into hole 1130, whereupon it rises and bursts out of the recovery pipe above ground.

Alternately, it is possible to use a net with a spring steel band, that expands it to block the pipeline, as shown in PCT Published Application WO 2004/059274

Once the sensor unit is recovered, the data recorded from its sensors in its recording unit is analyzed in known fashion. If the data has been transmitted by transmitter 120 before the sensor unit is recovered, the data analysis can begin even before recovery.

Figure 12:
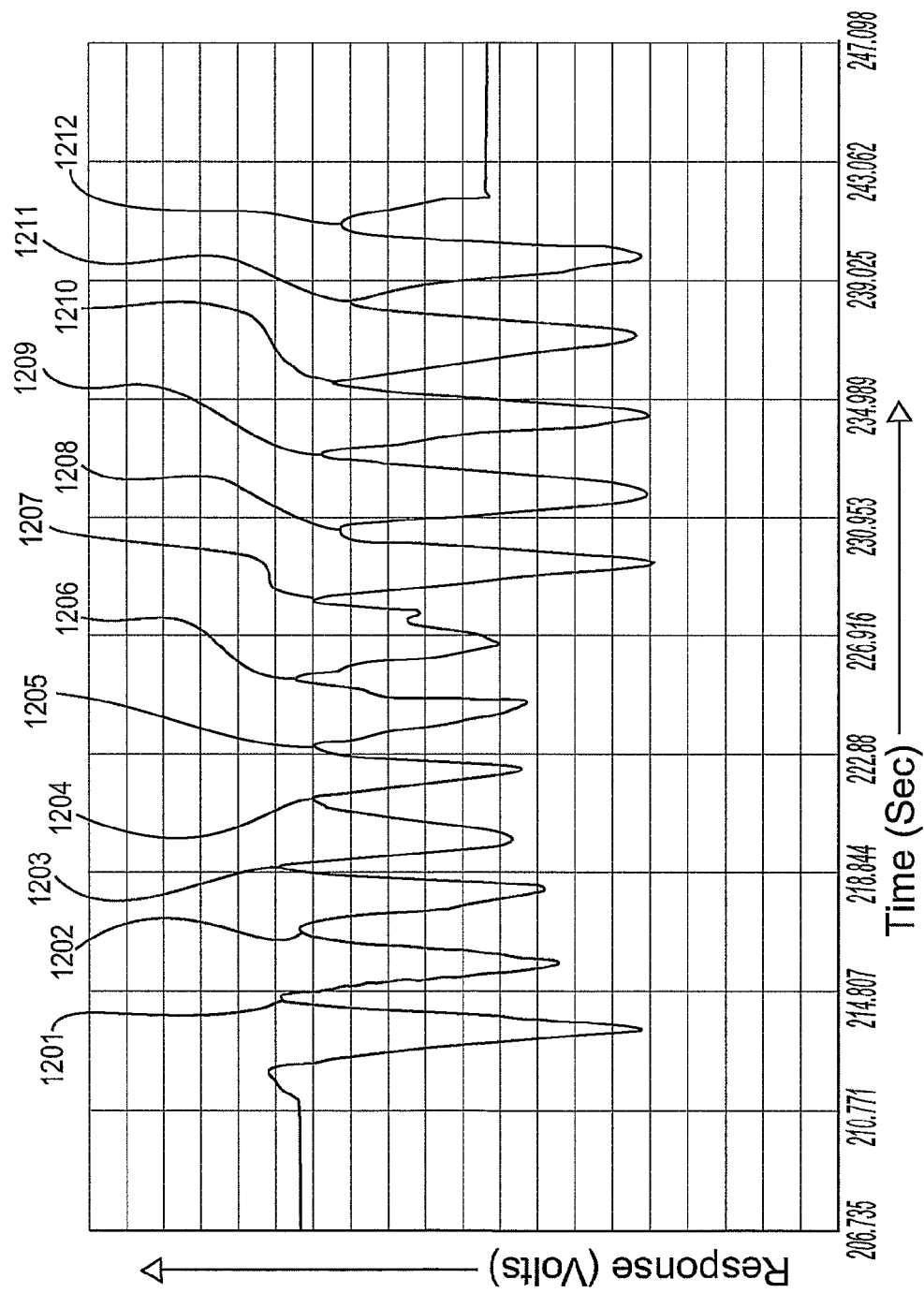
FIG. 12 shows the actual trace recorded by a magnetic sensor, showing the trace made as the sensor unit revolves while rolling along the pipeline.

FIG. 12 shows an actual trace made by a singe magnetometer as a spherical sensor unit having a circumference of 2 feet moved along a pipe. A pattern of regular peaks and troughs is seen. The peaks have been numbered 1201-1212 for clarity. Each peak represents the completion of a revolution. It is therefore easily seen from the graph that the sensor unit traveled 24 feet. The abscissa of the graph is elapsed time in seconds, and the ordinate is the voltage output of the magnetometer.

While the foregoing description and drawings have shown preferred embodiments of the invention, other embodiments will be evident to one skilled in the art, and are intended to be protected as well'.

What is claimed is:

1. A tether-free sensor unit of spherical or ellipsoidal shape with no motorized propelling means, for inspecting a pipeline which contains a moving liquid, which sensor unit comprises a sensor package containing a sensor to sense the number of revolutions of the sensor unit when such unit rolls along the bottom of the interior of the pipeline selected from at least one magnetic sensor and at least one accelerometer, and recording means for recording data sensed by said sensor, said sensor unit being of greater density than the density of the liquid in the pipeline to be inspected, whereby it can roll along the bottom of the pipeline to be inspected.

2. A sensor unit as claimed in claim 1, in which said sensor is three magnetometers, arranged orthogonally to one another.

3. A sensor unit as claimed in claim 2, additionally comprising an acoustic sensor.

4. A sensor unit as claimed in claim 3, additionally comprising a ball shaped outer surround which surrounds and protects the sensor package.

5. A sensor unit as claimed in claim 1, additionally comprising a temperature sensor to sense the temperature of liquid surrounding the sensor unit.

6. A sensor unit as claimed in claim 1, additionally comprising an acoustic transmitter or transponder.

7. A sensor unit as claimed in claim 6, in which the transmitter or transponder transmits a range of frequencies.

8. A sensor unit according to claim 6, in which the transmitter or transponder emits at least one frequency above 20 KHz.

9. A sensor unit according to claim 6, in which the acoustic transmitter or transponder transmits a range of frequencies comprising a swept pulse, in a range between 1 KHz and 200 KHz, 10. A sensor unit as claimed in claim 6, additionally comprising a battery to power said recording means and the transmitter or transponder.

11. A sensor unit as claimed in claim 1, in which the sensor unit is spherical and has a diameter of less than half and greater than 1/10 of the diameter of the pipeline to be inspected.

12. A sensor as claimed in claim 1, in which the sensor unit is ellipsoidal and the length of its major axis is less than ½ of the diameter of the pipeline to be inspected.

13. A method of inspecting a pipeline which contains flowing liquid, comprising;
   (a) providing a sensor unit which comprises a package containing a sensor selected from at least one magnetic sensor and at least one accelerometer, and means for recording data sensed by said sensor, said sensor unit being of greater density of the liquid in the pipeline to be inspected, and
   (b) allowing the sensor unit to be rolled along the bottom of the interior of the pipeline by the flow of the liquid, while recording a signal representative of the number of revolutions that the surface of the sensor unit has made.

14. A method as claimed in claim 13, in which the sensor unit comprises an acoustic transmitter or transponder, and the method includes emitting signals from the transmitter or transponder and receiving such signals at least one location along the pipeline.

15. A method as claimed in claim 14, in which signals are emitted at a frequency above 20 KHz.

16. A method as claimed in claim 13, in which signals are emitted at a range of frequencies comprising a swept pulse, in a range between 1 KHz and 200 KHz.

17. A method as claimed in claim 13, in which said sensor is three magnetometers, arranged orthogonally to one another.

* * * * *